United States Patent [19]

Samuels et al.

[11] 4,187,712
[45] Feb. 12, 1980

[54] HEMOSTATIC CLIP APPLICATOR

[76] Inventors: Peter B. Samuels, 14708 Sutton St., Sherman Oaks, Calif. 91403; Ernest C. Wood, 2461 Ivanhoe Dr., Los Angeles, Calif. 90039

[21] Appl. No.: 966,321

[22] Filed: Dec. 4, 1978

Related U.S. Application Data

[62] Division of Ser. No. 786,021, Apr. 8, 1977, Pat. No. 4,146,130.

[51] Int. Cl.² .............................................. B21D 7/06
[52] U.S. Cl. ......................................... 72/410; 81/341
[58] Field of Search ............... 72/410, 409; 29/243.56; 128/325, 334 R, 335, 346, 340, 354; 81/341, 315, 319, 320, 364, 365, 366; 206/340

[56] References Cited
U.S. PATENT DOCUMENTS

| | | | |
|---|---|---|---|
| 3,270,745 | 9/1966 | Wood | 128/325 |
| 3,326,216 | 6/1967 | Wood | 128/325 |
| 3,439,522 | 4/1969 | Wood | 72/410 |
| 3,631,707 | 1/1972 | Miller | 72/410 |
| 3,732,719 | 5/1973 | Pallotta | 72/410 |
| 3,867,944 | 2/1975 | Samuels | 128/325 |
| 4,073,179 | 2/1978 | Hickey | 72/409 |

*Primary Examiner*—Francis S. Husar
*Assistant Examiner*—Gene P. Crosby
*Attorney, Agent, or Firm*—McDougall, Hersh & Scott

[57] ABSTRACT

A hemostatic clip applicator is provided with a locking mechanism preventing the accidental release of the clip before its application to a blood vessel. The locking mechanism includes a locking bar dimensioned to pass into aligned slots to prevent opening of the jaws beyond a selected distance.

3 Claims, 15 Drawing Figures

HEMOSTATIC CLIP APPLICATOR

This is a division, of application Ser. No. 786,021, filed Apr. 8, 1977, now U.S. Pat. No. 4,146,130.

BACKGROUND OF THE INVENTION

This invention relates to mechanisms useful in the strangulation of tubular members. Specifically, it is directed toward devices including hemostatic clips useful in the strangulation of blood vessels and other fluid ducts in the human body.

The particular application of this invention to the strangulation of blood vessels will serve as an illustration of the inventive concepts enclosed herein. It will be appreciated, however, that the mechanisms embodying the concepts of this invention can be adapted for the closing of other tubular structures at intermediate points as well as near their open ends.

In the course of a surgical operation, a surgeon must often sever one or more blood vessels. It is desirable to provide means for closing the ends of the severed vessels, at least until the end of the operation, to stop bleeding that could interfere with the performance of the operation as well as present unnecessary risks to the patient.

Conventional means for closure consist of ligatures or the like tied about the individual vessels at the desired point of strangulation. The customary technique provides for the separate clamping of each vessel after the incision has been made. After clamping the vessels, a ligature is secured about each vessel providing closure and permitting the removal of the clamps. In some instances a great number of vessels must be severed after requiring one or more hours for proper closure at which point the operation may proceed. It will be apparent that an improved technique for closure will not only obviate the excessive expenditures of time by the surgeon and his assistants under conventional practice but also the dangers to the patient inherent in any delay.

It is an object of this invention to provide mechanisms for use in the strangulation of blood vessels and the like whereby the time required for closure is materially reduced and whereby bleeding can be terminated without the use of the excessive combination of clamping and tying operations.

It is a more particular object of this invention to provide improved mechanisms for the strangulation of blood vessels and the like whereby the blood vessels may be sealed off in a highly efficient manner to prevent bleeding during an operation and whereby the operation can proceed with a minimum loss of time as well as blood thereby to maintain conditions most favorable to the patient.

Hemostatic clip systems are known in the prior art. In particular, the closest prior art of which applicants are aware include the following U.S. patents, all of which were developed by one or both of the named inventors of the present application: U.S. Pat. Nos. 3,326,216, 3,363,628, 3,270,745, 3,439,522, and 3,439,523. In each of these referenced patents there is disclosed a hemostatic clip, a clip applicator and a cartridge in which the clip is stored until withdrawn by the applicator for use. With respect to the cartridge and clip a problem with the prior devices has been the tendency of the clip to bind against the central support of the cartridge during removal of the clip therefrom. Since the cartridge is usually made of plastic while the clip is usually formed of stainless steel or the like, if the clip is too securely tensioned on the central support it will stick or bind and is difficult to remove from the cartridge.

Removal of the clip is even more troublesome if the clip is provided with raised friction surfaces on the inside thereof, which surfaces are especially beneficial for insuring that the clip remains securely attached to a blood vessel. Often where such a raised occlusive surface is provided plastic will be torn away from the central binding post during removal of the clip from the cartridge. This is highly undesirable. As a result of these problems, it has not heretofore been practical to provide the desirable raised occlusive surfaces on the inside of the clip. Instead, as illustrated in the referenced patents, various recessed clip designs have been utilized.

According to one aspect of the present invention an improved cartridge is provided in which the clip is not secured in the cartridge by intimate engagement with the central post. Instead, it is maintained within its compartment by a strip of tape or other fabric placed across the top of the compartment and then severed. The flap end of the severed tape acts as a "swinging door" to retain the clip until needed and then to permit easy removal from the compartment.

Having solved the problems inherent in the prior art cartridges it then becomes possible to provide improved hemostatic clips which can have the desired raised occlusive surfaces on their internal surfaces.

Another feature of the present invention is the provision of an improved clip applicator. A serious problem with the clip applicator is the normal tendency of the surgeon to anticipate application of the clip to a blood vessel by slightly and unconsciously opening the scissor-like device as it is being used to guide the clip in place over the blood vessel. When this occurs, in the absence of any restraining devices, the clip is prematurely released from the jaws of the applicator. To prevent this from occurring it has been known in the prior art (see U.S. Pat. No. 3,326,216) to try and limit the outward movement of the jaws. In the patent just referenced this was accomplished by use of a leaf spring connected to one leg of the instrument and engaging a limiting hook provided on the opposite leg. While somewhat successful a more secure way of limiting the jaw travel is desired.

It is accordingly an object of the present invention to provide an improved system for applying hemostatic clips.

A further object of the invention is to provide an improved cartridge for hemostatic clips in which the cartridge is not secured to the central binding post.

Another object of the invention is to provide an improved hemostatic clip having a plurality of raised projections on the internal surfaces thereof.

A further object of the invention is to provide an improved clip applicator which securely limits the travel of the applicator jaws during use to prevent loss of the clip.

Other objects and advantages of the invention will be apparent from the remaining portion of the specification.

DETAILED DESCRIPTION

Figure 1:
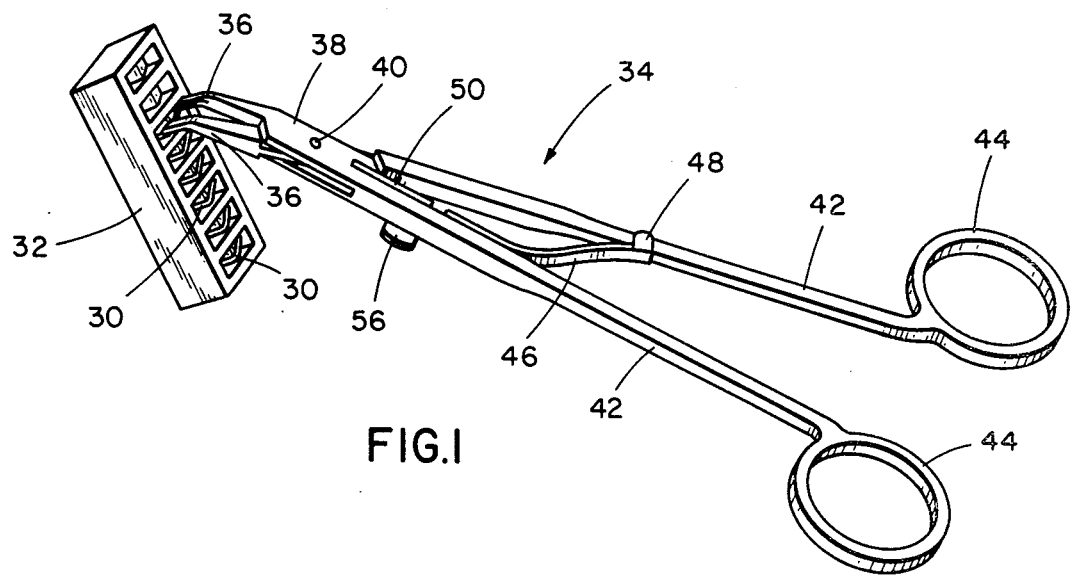
FIG. 1 is a perspective view of the applicator and a clip cartridge according to a first embodiment thereof.
Figure 2:
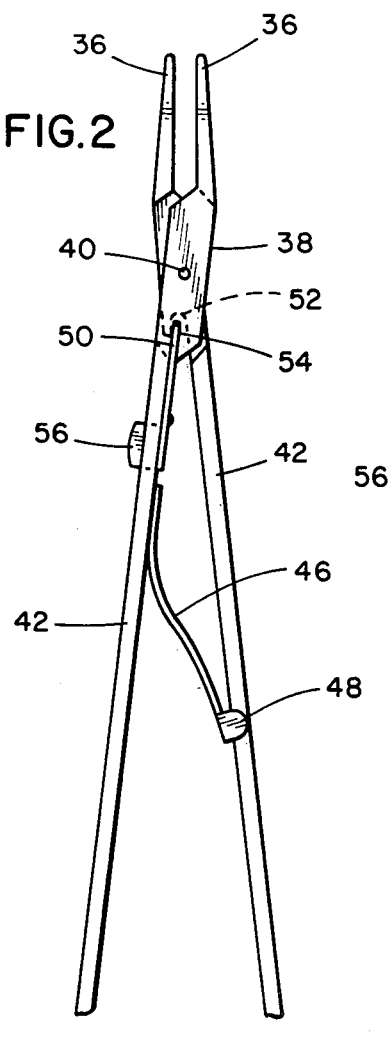
FIGS. 2 and 4 are front elevational views of the applicator according to the invention.
Figure 8:
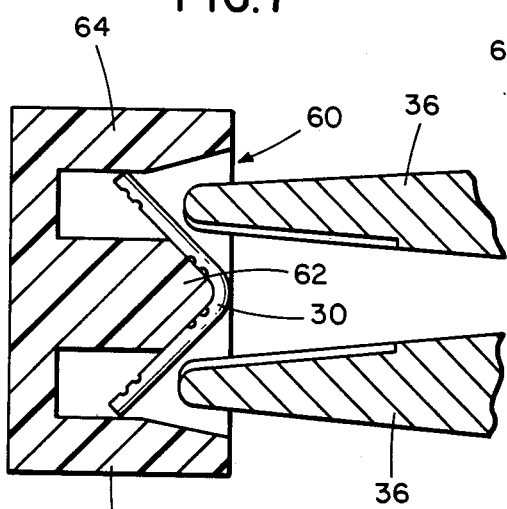
FIG. 8 is an enlarged sectional view illustrating the manner of removing a clip from the cartridge.
Figure 11:
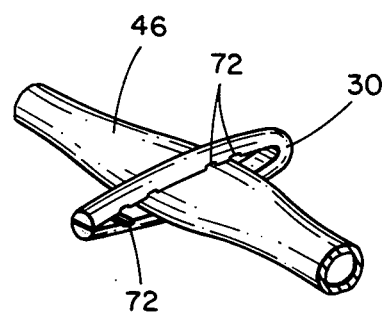
FIG. 11 is a perspective view illustrating the manner in which the clip is applied to a blood vessel.

Referring to FIG. 1, the clip system according to a first embodiment of the invention is illustrated. A plurality of clips 30 are provided in a clip cartridge 32. The clips are secured within the cartridge by the spring tension of the clip as illustrated in FIG. 8. When it is desired to remove a clip from the cartridge for subsequent application to a blood vessel the applicator device 34 is inserted into one of the compartments of the cartridge to withdraw a clip therefrom. The applicator device is a scissor-like instrument having a pair of exposed jaws 36 secured by a "boxed hinge" 38 including hinge pin 40. Attached to the jaws are elongated arms 42, each terminating in a finger hole 44 whereby manual operation of the applicator is accomplished. A clip removed from the cartridge by the applicator 34 is placed over a blood vessel 46 (FIG. 11) and the clip is compressed thereon to close off the vessel.

Referring to FIGS. 2 through 6, the construction details of the applicator according to the invention are illustrated. The jaws 36 are biased to the opened position illustrated in FIG. 2 by a leaf spring 46 attached to one of the arms 42 and extending to a point of engagement with the opposite arm. A follower 48 insures that the leaf spring glides along the opposite arm during movement of the jaws.

As indicated in the background portion of the specification, when a clip is secured between the jaws of the applicator (see FIG. 10) it is maintained in a set of grooves by slight pressure of the clip against the jaws. If the jaws are not maintained at the correct spaced distance the clip will be prematurely crimped or alternatively will drop from between the jaws. Accordingly, it is necessary to maintain the jaws at a correct fixed position during pick up of a clip and subsequent placement of the clip in position over a blood vessel. The leaf spring 46 provides one portion of the positioning structure by normally maintaining the applicator open a selected amount.

Figures 3, 6:
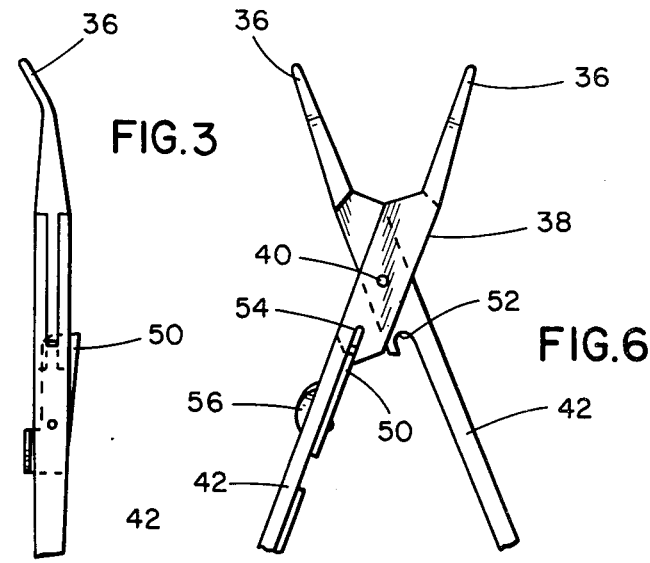
FIG. 3 is a side elevation of the applicator.
FIG. 6 is a front elevation of the applicator with the locking means disengaged.
Figures 4, 5:
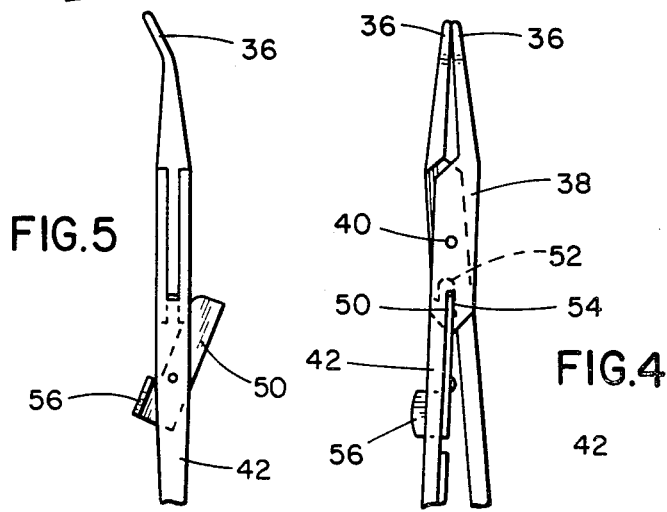
FIG. 5 is a side elevation of the applicator in which the locking means is disengaged.

Preventing excessive opening of the jaws is accomplished by a locking bar 50 hingedly secured to one arm of the applicator. As best seen in FIG. 6, the arms 42 are provided with slots 52 and 54 at a point just below the hinge pin 40. These slots pass completely through the arms and are located so that when the jaws are at the correct spacing for the intended size of the clip to be used the slots 52 and 54 will be in vertical alignment. The locking bar 50 is then pivoted into the aligned slots where it serves to prevent subsequent outward movement of the jaws. Thus, during use of the instrument its jaws are maintained at precisely the correct spacing for picking up and placing a clip.

The spacing can be changed by manual application of pressure to the finger holes 44 when it is desired to crimp a clip onto a blood vessel. Upon release of pressure on the finger holes the leaf spring 46 returns the jaws to their initial position for application of additional clips. The locking bar 50 prevents outward movement of the jaws beyond the correct spacing by preventing pivoting of the arms away from the position wherein the slots 52 and 54 are in alignment.

Note the difference in the width of slot 52 as compared with slot 54. The width of slot 52 exceeds that of slot 54. This extra width permits sufficient inward movement of the jaws for clip crimping while permitting substantially no play beyond the point of correct clip spacing. The locking bar 50 is pivotable so that by movement of the locking bar out of the slots 52 and 54 the instrument may be opened for sterilization. A tab 56 may be provided on the locking bar to facilitate movement of the bar between its locked and released positions.

Figure 7:
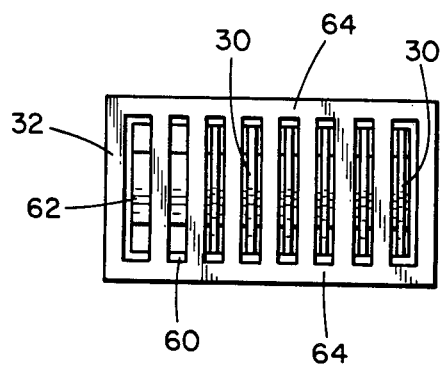
FIG. 7 is a plan view of the cartridge and clip according to a first embodiment.
Figure 9:
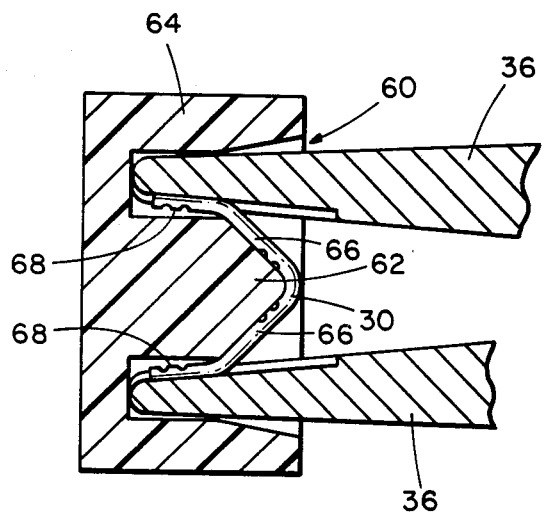
FIG. 9 is a view similar to FIG. 8.
Figure 12:
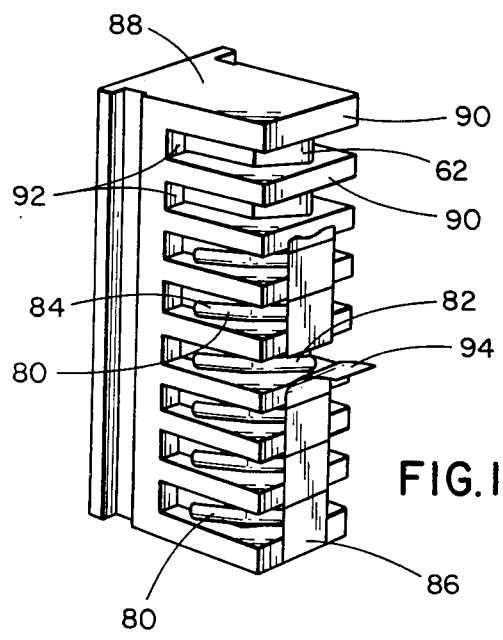
FIG. 12 is a perspective view of a cartridge and clip according to a second embodiment of the invention.
Figure 13:
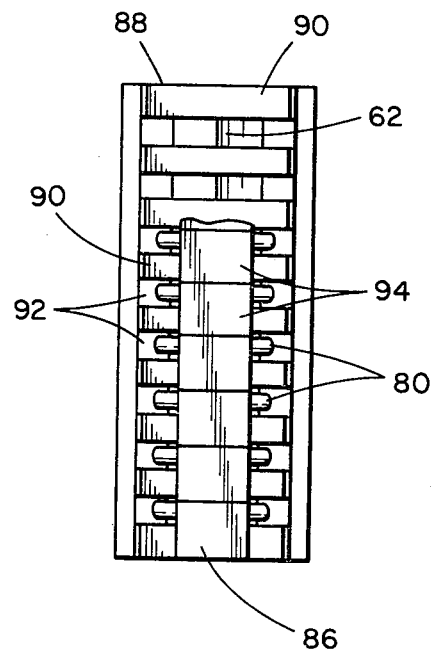
FIG. 13 is a plan view of the cartridge of FIG. 12.

Referring now to FIGS. 7 through 9, a cartridge according to a first embodiment of the invention is illustrated. In this embodiment a cartridge 32 has a plurality of clips provided therein. The clips are removed by inserting the applicator into the various compartments, such as, compartment 60. The clips are secured within the compartment by virtue of the resiliency of the material from which they are constructed. Typically, clip 30 will be formed of stainless steel or similar material. The clip is securely positioned in intimate contact with a central binding post 62 while the ends of the clip press against the sides 64 of the compartment. In this manner the clip is pinioned in place and maintained in correct position for removal.

Figure 10:
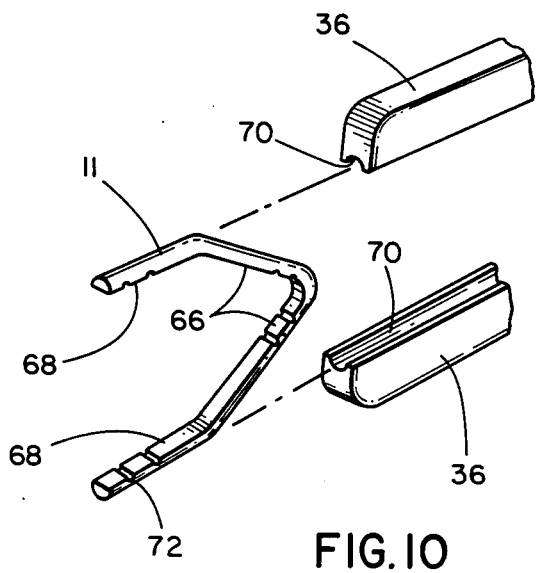
FIG. 10 is a perspective illustrating the manner in which a clip is received in the channels of the applicator jaws.

As indicated in FIGS. 9 and 10, the clip may conveniently be described as having a V-shaped portion 66 beginning at its midpoint and extending outwardly to the beginning of a parallel portion 68 in which the ends of the clip are parallel to each other and in opposed relation. The clip acquires this shape when the jaws 36 are inserted into the compartment for the purpose of removing the clip therefrom. When this occurs, as best illustrated in FIG. 9, the jaws engage the parallel portions 68 of the clip forcing them inwardly away from the ends of the cartridge 64. The clip may then be easily removed from the cartridge. The clip is maintained between the jaws 36 in a pair of opposed grooves 70 due to the locked position of the jaws.

As indicated in the background portion of the specification, a problem with cartridges in the past has been the tendency of the clip to stick to the central binding post 62 or to scrape off material therefrom. According to this first embodiment of the invention the points of contact of the clip with the central binding post are significantly reduced thereby alleviating this problem. In fact, the parallel leg portion 68 does not touch the central binding post at all during storage and removal. Only the V-shaped portion 66 is in contact with the binding post. Accordingly, it is possible to provide raised occlusive surfaces on the parallel leg portions of these clips without the problems associated therewith in the prior art. In the drawings, however, the clip has been illustrated as having recessed occlusive surfaces 72 which, although effective for maintaining the clip in position on a blood vessel, are not as effective as raised surfaces.

Figure 14:
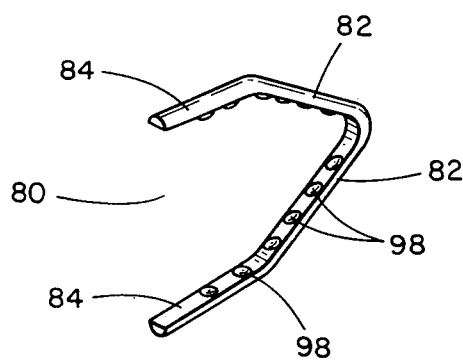
FIG. 14 is a perspective view of the clip according to another embodiment of the invention.
Figure 15:
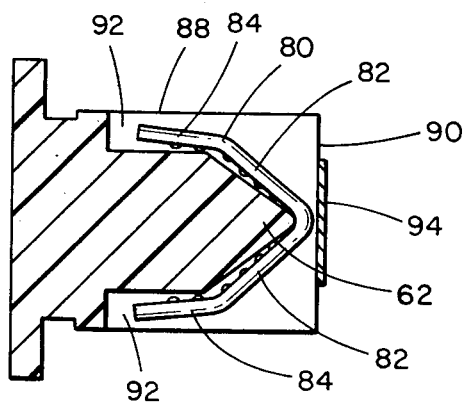
FIG. 15 is an enlarged sectional view of the cartridge and clip according to the second embodiment.

Referring now to FIGS. 12 through 15, a clip and cartridge according to a second and preferred embodiment of the invention is disclosed. In this embodiment an improved cartridge is provided in which the clip is not secured against the binding post 62. Instead, the clip is permitted to move within the compartment although it remains in the general position illustrated by virtue of the presence of the binding post 62. The clip, as indicated in FIG. 14, is preformed to the desired shape. That is, the clip 80 has a preformed V portion 82 and parallel leg portion 84. The dimensions of the clip slightly exceed the dimensions of the binding post (FIG. 15) so that the clip is free to move loosely about the binding post 62.

In order to prevent the clip from dropping out of the cartridge, a narrow strip of fabric 86 is stretched across the top of all of the compartments of the cartridge 88. The fabric is then severed between the walls 90 which define the clip compartments 92. The severed fabric permits easy removal of the clip by the applicator when desired but in the absence of insertion of the applicator acts to prevent loss of the clip from the compartment. By analogy the loose end 94 of the fabric may be thought of as a swinging door.

The strip of fabric can be a tape having adhesive on one side thereof in which case it is positioned along the length of the cartridge top and then severed either in the middle between adjacent partitions 90 or preferably closer to one partition than the other so as to leave a large flap portion 94 for retaining the clip in place. Alternatively, in place of tape a fabric, such as a plastic strip, could be glued only to the tops of the partitions 90 and then the same severing process utilized. The latter procedure, although more difficult to accomplish, has a slight advantage in that it avoids the possibility of the clip contacting the adhesive on the underside of the tape and hindering clip removal. In practice this has not been found to be a serious problem but it can be avoided by use of the second method of gluing a fabric material over the top of the cartridge. A suitable material is plastic although other material can serve the purpose.

Referring to FIG. 14, a clip suitable for use with the cartridge of the second embodiment is illustrated. By virtue of the advantage of the second embodiment it is now possible to provide a clip which has raised projections 98 on both the V portion 82 and the parallel portions 84 of the clip. This is possible, of course, because the clip no longer is secured against the binding post 62 either before clip removal or during clip removal and, therefore, there is no danger of the projections 98 binding on the post 62 or scrapping material away from the binding post.

While the FIG. 14 clip is illustrated as having a plurality of projections arranged in a single line along the inner face of the clip, it should be recognized that various other raised projections can be utilized to produce a good occlusive surface on the interior of the clip. For example, the raised projections could be triangles, squares, circles or combinations of these configurations depending upon a particular application. Further, for large and medium large clips double rows of raised projections could be used. The distinction to be borne in mind between this embodiment and the FIG. 8 embodiment is that raised projections may be provided on the inner surface of the clip since there is no longer the danger of the of the clip biting into the binding post during clip removal.

While we have shown and described embodiments of this invention in some detail, it will be understood that this description and illustrations are offered merely by way of example, and that the invention is to be limited in scope only by the appended claims.

We claim:

1. In a clip applicator including a pair of opposed crimping jaws adapted to receive and crimp a hemostatic clip, said jaws secured for relative movement of a boxed hinge, arms having finger holes at the end thereof attached to said jaws to permit manual relative movement of said jaws and a spring means for biasing the jaws to an open position in the absence of manual pressure, the improvement comprising:

means for preventing said jaws from opening more than a selected distance, said selected distance corresponding to the correct distance for receiving a clip in said jaws, said preventing means including:
(a) a locking bar secured to one of said arms,
(b) slots provided through the arm portions of said boxed hinge, said slots being dimensioned and positioned relative to each other and said locking bar that when said jaws are at said selected distance said slots are in alignment, said locking bar being dimensioned to pass into the aligned slots to thereafter prevent opening of said jaws beyond said selected distance.

2. The device according to claim 1 wherein one of said slots is wider than the remaining slot to permit movement of said jaws to a clip crimping position while still preventing opening of said jaws beyond said selected distance.

3. The device according to claim 1 wherein said locking bar is pivotally mounted to said one arm whereby it may be removed from said slots to permit opening of said jaws for cleaning.

* * * * *